(12) United States Patent
Mishkin et al.

(10) Patent No.: US 6,823,881 B1
(45) Date of Patent: Nov. 30, 2004

(54) SINGLE CHANNEL, RETRACTABLE NEEDLE DIALYZER HEADER CLEANING DEVICE

(76) Inventors: Gary Mishkin, 8716 Tuckerman La., Potomac, MD (US) 20854; Mark Mishkin, 3000 S. Randolph St., #212, Arlington, VA (US) 22206

( * ) Notice: Subject to any disclaimer, the term of this patent is extended or adjusted under 35 U.S.C. 154(b) by 165 days.

(21) Appl. No.: 09/918,541

(22) Filed: Aug. 1, 2001

(51) Int. Cl.⁷ .................................................. B08B 3/00
(52) U.S. Cl. ................................... 134/167 R; 134/179
(58) Field of Search ......................... 134/166 R, 167 R, 134/168 R, 172, 176, 177, 179; 210/636, 646

(56) References Cited

U.S. PATENT DOCUMENTS 4,375,413 A    3/1983 Geel et al. .................. 210/636
6,050,278 A    4/2000 Arnal et al. ............. 134/167 R
6,192,900 B1 * 2/2001 Arnal et al. ................ 134/22.1

* cited by examiner

Primary Examiner—Frankie L. Stinson
Assistant Examiner—Joseph L. Perrin
(74) Attorney, Agent, or Firm—Browdy and Neimark, P.L.L.C.

(57) ABSTRACT

A dialyzer header cleaning device composed of: a housing having two opposed ends and delimiting a passage that extends in a flow direction between the two ends; a connecting element disposed at a first end of the housing for connection to the header; and a flow directing element having a fluid inlet end retained in the passage and a fluid outlet end. The flow-directing element has a cleaning position in which the fluid outlet end extends into the header when the first end of the housing is connected to the header. The flow-directing element is constructed to rotate about an axis that extends in the flow direction in response to a flow of liquid between the fluid inlet end and the fluid outlet end, and to eject at least one liquid stream from the fluid outlet end in a direction transverse to the flow direction.

14 Claims, 4 Drawing Sheets

SINGLE CHANNEL, RETRACTABLE NEEDLE DIALYZER HEADER CLEANING DEVICE

BACKGROUND OF THE INVENTION

The present invention relates to devices for cleaning dialyzer headers.

Hemodialysis is an extracorporeal therapy whereby blood is pumped out of the body and through a dialyzer, also know as an artificial kidney, and returned back to the body. The dialyzer is composed of two regions: a blood region and a dialysate region, the two regions being separated from one another by a filter-like membrane possibly composed of hollow fibers or flat sheets. The membrane is porous and permits water and small and middle weight molecules to pass across.

The blood that is pumped out of the body is pumped through the blood region of the dialyzer. Dialysate, a fluid that contains the electrolytes the body needs and bicarbonate to aid in acid base balance in the body, is caused to flow through the dialysate region in counter current to the blood flow through the blood region. Toxins in the blood pass across the membrane from the blood region into the dialysate region by diffusion or convection. Electrolytes and bicarbonate pass from the dialysate in the dialysate region across the membrane into the blood region in a similar manner.

Many dialysis facilities reuse the dialyzers in order to save money. The costs associated with dialyzer reuse include: reuse space, water and electricity, the cost of machines specifically designed to reprocess the dialyzers and reprocessing chemicals, and employee salaries.

The steps involved in dialyzer reuse vary from clinic to clinic. However, certain steps are universal. After completion of a dialysis treatment, the first step in the reuse process is to rinse any residual blood out of the dialyzer. For this purpose, the dialyzer is connected to a water supply and fluid is flushed through the blood and/or dialysate regions. This process rinses out many of the large particles and blood components left in the dialyzer. After the dialyzer is rinsed the dialyzer is then reprocessed.

Although many clinics throughout the world manually reprocess the dialyzers, there are currently many machines, such as those marketed by Minntech Corp. under the trade name Renatron, Mesa Medical under the trade name Echo, etc., that are capable of automatically reprocessing dialyzers.

Automatic reprocessing is similar to manual reprocessing. In automatic reprocessing, the dialyzer is connected to the reprocessing machine by both blood ports (arterial and venous) and both dialysate ports. Water or other cleaning liquid is then flushed through both regions of the dialyzer to further rinse away blood products. This is done in several steps. The cleaning step of dialyzer reprocessing is performed by flushing water mixed with a cleaning agent such as a bleach or peroxyacetic acid, through the dialyzer. This is also performed in other steps including a backflush. The backflush process rinses the water and cleaning agent from the dialysate side through the membrane to the blood region and out of the blood region ports. This backflush process can loosen and remove any blood or blood products that are adhered to the inner wall of the dialyzer fibers.

Most reused dialyzers are taken out of use, or fail, because the volume of the dialyzer, i.e., the volume of the blood compartment, has dropped below acceptable levels. Any blood products that block the fibers will reduce the volume of the dialyzer. Very rarely does a dialyzer fail due to inadequate results on a leak test.

The headers of a dialyzer are the part of the dialyzer where the blood enters and leaves the dialyzer. During dialysis, as blood is pumped through the dialyzer, microclots, fibrin and other biologic products react with the dialyzer and may also react with the extracorporeal circuit consisting of blood lines, the pump and the dialysate compartment. These biologic products are commonly found accumulated in the headers of the dialyzer, many times forming a sheet that can completely block the openings to the fibers and blood region of the dialyzer.

These biologic products must be removed from the dialyzer in order to obtain adequate blood volume during reuse testing. Currently, flushing water is the most common method used to remove the biologic products from the header of the dialyzer. However, due to the design of the dialyzer header, this is not always effective. Some dialyzers have header caps that can be unscrewed to facilitate cleaning. However, due to concerns of cross contamination, the complexity of properly reassembling such a dialyzer and damage to the dialyzers, removing the header caps is discouraged.

U.S. Pat. No. 6,050,278 by Arnal et al and U.S. Pat. No. 4,375,413 by Geel et al disclose dialyzer cleaning devices having needles for injecting water into the dialyzer head. The device disclosed by Geel et al has a single solid piece for spraying water, which is not capable of rotating or retracting. Arnal et al disclose a needle that may oscillate and retract. Oscillation is effected by a gear assembly that undergoes reciprocal motion created by a pulsating fluid. Thus, this is a structurally complex device.

BRIEF SUMMARY OF THE INVENTION

The present invention provides a novel device that improves cleaning of dialyzer headers.

Specifically, the invention provides a dialyzer header cleaning device comprising: a housing having two opposed ends and delimiting a passage that extends in a flow direction between the two ends; a connecting element disposed at a first end of the housing for connection to the header; and a flow directing element having a fluid inlet end retained in the passage and a fluid outlet end, the flow directing element having a cleaning position in which the fluid outlet end extends into the header when the first end of the housing is connected to the header, wherein the flow directing element is constructed to rotate about an axis that extends in the flow direction in response to a flow of fluid between the fluid inlet end and the fluid outlet end, and to eject from the fluid outlet end fluid streams that are directed transverse to the flow direction; and/or the flow directing element is movable parallel to the flow direction between the cleaning position and a back flush position n response to flow of fluid through the passage from the flow outlet end toward the fluid inlet end to provide a back flush flow path through the passage and around the flow directing element.

DETAILED DESCRIPTION OF THE INVENTION

The present invention provides a device for cleaning a dialyzer header, which is typically a region delimited by a header cap and one end of the main body of the dialyzer, which contains the dialysate and blood regions. The device according to the invention can be screwed onto the dialyzer header and has a hollow pin, or needle, preferably in a funnel form, that drops into the header and produces a stream or streams of water when connected to a water supply. The streams are preferably directed in a plane parallel to the end surface of the header cap, or can be directed at a small angle to that plane, so as to dislodge biologic products so that they can be easily washed out of the dialyzer. The needle can be made to rotate manually or can be made to spin by the pressure of the incoming water, in order to rinse the entire periphery of the header, or header cap, adjacent its end surface.

This device will also permit the back flushing of water and biologic products out of the header when fluid is flushed from the other side of the dialyzer. This flow of fluid from the opposite side pushes the needle out of the header, while assuring that the needle remains within the device, so that blood products can be washed out of the dialyzer. As water is flushed from the opposite side, large clots will have the required space to be flushed out of the dialyzer. To aid in the removal of large clots, propellers may be put on the pin device acting as a blade to macerate the clots as they pass.

Figure 1:
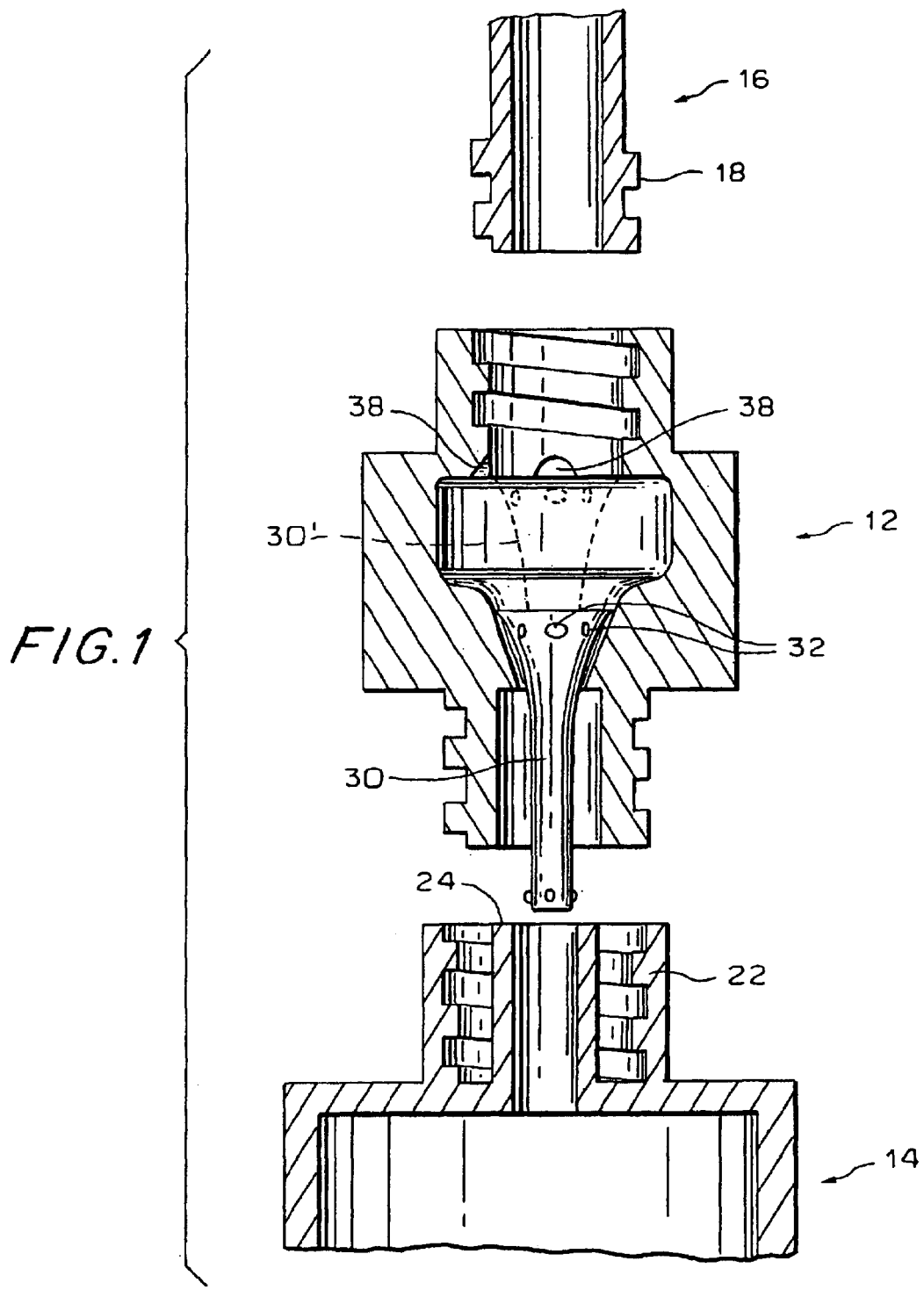
FIG. 1 is an elevational cross-sectional view illustrating a first preferred embodiment of the invention.

FIG. 1 shows a preferred embodiment of a header cleaning device 12 according to the invention, together with a portion of a dialyzer header cap 14 and a line 16 provided with a connector 18 for supplying cleaning water or other fluid and receiving backflush liquid.

Device 12 is essentially constituted by a housing having threaded connecting portions at both ends for connection to dialyzer header cap 14 and connector 18, device 12 being formed to have a passage that extends between the ends. As shown, the passage includes a cylindrical main chamber and a tapered section that extends from the chamber to the end provided for connection to header cap 14. A needle 30 having a funnel shape, as described above, is retained via its flared upper end in the tapered section of the passage. Needle 30 is shown not in cross section in FIG. 1. The structural details and the operation of needle 30 will be described below.

Header cap 14 is provided with a coupling arrangement for connection to a dialyzer system, the coupling arrangement including, by way of example, an outer luer flange 22 and an inner luer flange 24. The inner surface of flange 22 is threaded. Connector 18 is externally threaded.

Figure 2:
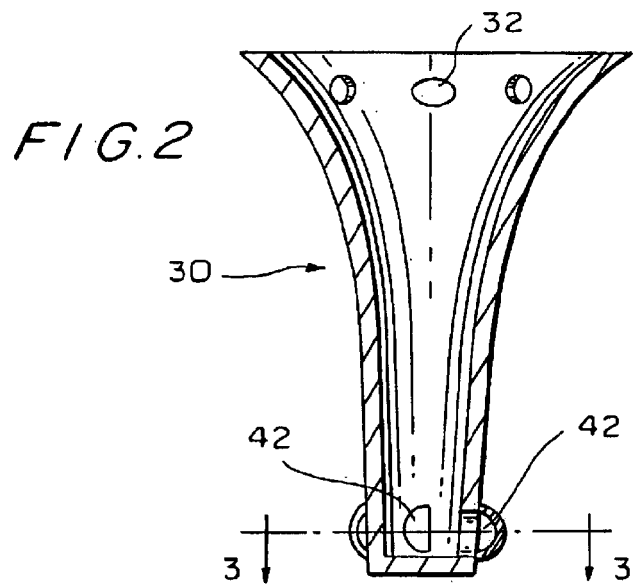
FIG. 2 is an elevational, cross-sectional view of one component of the device of FIG. 1.
Figure 3:
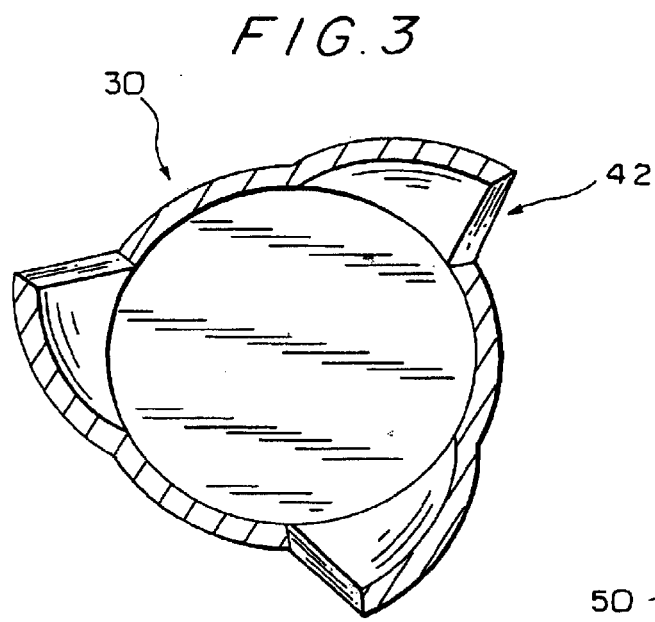
FIG. 3 is a cross-sectional view taken along the line 3—3 of FIG. 2.

FIGS. 2 and 3 show needle 30 in greater detail, and in particular show the preferred form of outlet openings 42 at the fluid outlet end of needle 30. Outlet openings 42 have the form of nozzles that produce streams or sprays directed tangentially to the outer wall of needle 30. Thus, cleaning liquid is ejected tangentially to the outer wall of needle 30 and produces a reaction force that rotates needle 30 about its longitudinal axis. This, in turn, causes the paths followed by the cleaning liquid streams or sprays to be rotated about that longitudinal axis, assuring impact against the entire periphery of the interior wall of cap 14. One or more openings may be provided, three openings being shown only by way of example. The resulting streams or sprays impact against the periphery of the interior of cap 14, and particularly against the corner between the axial end and the peripheral wall of cap 14 and across the top of the dialyzer, to dislodge blood products.

Figure 4:
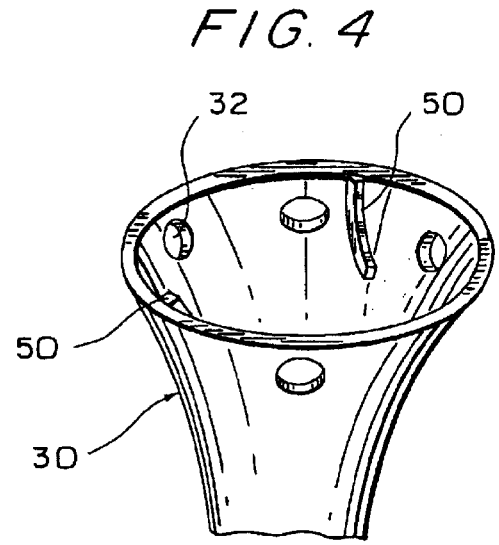
FIG. 4 is a perspective detail view of a portion of a modified version of a component of the device shown in FIGS. 1–3.

As shown in FIG. 4 the flared upper end of needle 30 may have grooves or lands 50 that extend at an angle, for example along helical paths, to aid in the rotation of the needle. It is also possible to have a propeller or similar structure that acts as blades to macerate or break up the clots and blood products as the needle spins.

Figure 5:
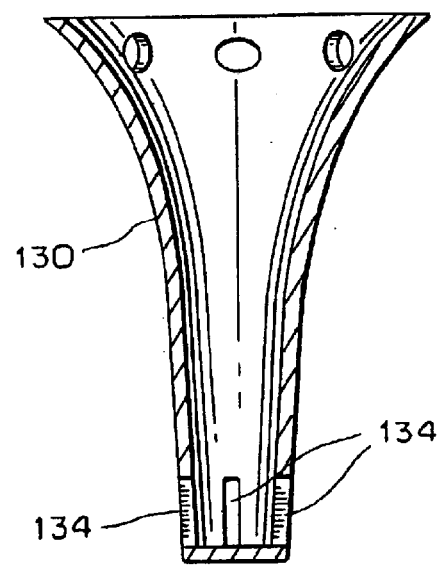
FIGS. 5 and 6 are cross-sectional views of two further embodiments of the component.

FIG. 5 illustrates another embodiment of a needle 130 for use in a device according to the invention. In this embodiment, the tip of needle 130 has one or more slits 134 that will direct streams perpendicular to the common longitudinal axis of the device and needle 130 and thus parallel to end surface of header cap 14. Slit or slits 134 in the tip of needle 130 may extend perpendicular to the dialyzer header cap end surface, as shown, resulting in a spray perpendicular to the header in order to dislodge blood products. The length and angle of the slits are preferably selected to maximize cleaning capability.

Figure 6:
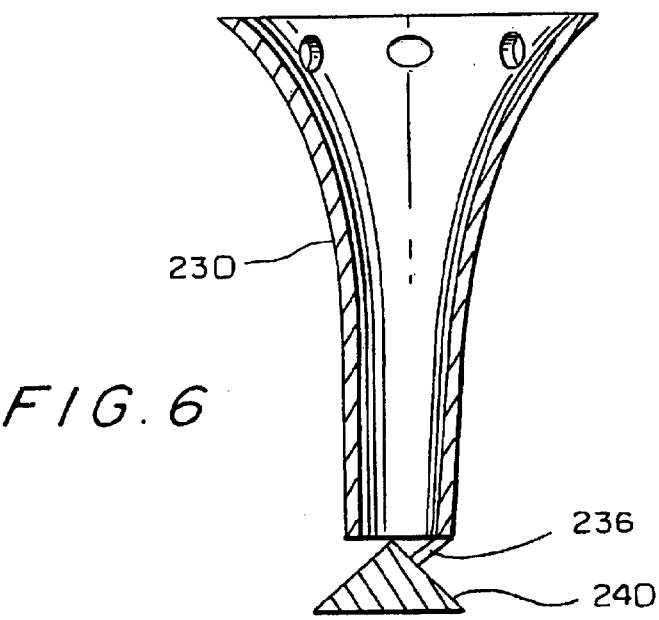

FIG. 6 illustrates a further embodiment of a needle 230 for use in a device according to the invention. In this embodiment, the outlet end of needle 230 is open and is connected via a thin bar 236 to a diverting member 240 having a conical diverting surface that forms an angle of the order of 45° with the longitudinal axis of needle 230. This arrangement produces a 360° spray in a plane essentially perpendicular to the longitudinal axis of needle 230 to clean the entire periphery of the interior of cap 14 simultaneously. The gap between the outlet end of needle 230 and member 240 may be made relatively small to produce a high velocity liquid jet.

Reverting to FIG. 1, to clean header cap 14, device 12 may be provided with any one of the needles described above and then is connected to header cap 14 and connector 18 and a flow of cleaning liquid is supplied to device 12 from line 16. This liquid flows downwardly, with respect to the orientation shown in FIG. 1, and assures that the needle will be in its cleaning position, shown in solid lines in FIG. 1, with the lower extremity, or tip, of the needle extending into the dialyzer header.

If the device is provided with needle 30, the flow of liquid will cause the needle to spin due to the design of the needle, as described above. The resistance to spin caused by contact between the flared upper edge of needle 30 and the wall of the passage formed in device 12 will be minimized by making the surface area of contact therebetween as small as possible. Spinning of needle 30 may also be aided by providing openings 32 in needle 30 adjacent the fluid inlet of the needle to allow some fluid to pass laterally out of the path enclosed by needle 30 so as to impose a lifting force that reduces or neutralizes the friction force between needle 30 and the wall of the passage formed in device 12, thereby permitting the needle to rotate freely.

When needle 130 or 230 is used, it will not spin in response to the flow of liquid therethrough. However, particularly if needle 130 is used, according to another embodiment of the invention, which will be described below with reference to FIG. 7, the housing containing the needle can be rotated manually to assure thorough cleaning of the interior surfaces of cap 14.

The fluid that enters the connected dialyzer header travels through the dialyzer and out of the second dialyzer header (not shown) at the opposite end of the dialyzer.

Once all blood products appear to have been adequately dislodged from the first header, the flow of cleaning liquid is stopped and device 12 is disconnected. Device 12 may then be reconnected to the opposite header cap and the cleaning operation can then be repeated, this time with cleaning liquid flowing in the opposite direction through the dialyzer.

Blood products that were dislodged during the first cleaning operation but not removed from the dialyzer will be easily flushed out when cleaning liquid is delivered to the header at the opposite end of the dialyzer. Blood products dislodged in the second header by connection of the device thereto, can be removed by again connecting device 12 to the first cap and again causing cleaning liquid to flow through device 12.

Alternatively, after dislodging blood products from the first header cap, device 12 can remain connected to the first header cap and the water supply line can be connected to the opposite, or second, header cap. The resulting reverse flow, or back flush flow, will force needle 30, 130, or 230 away from the header cap to which it is connected and into the passage in device 12, so that the blood products can be flushed out of the dialyzer header cap, through device 12 and into a sink. When this flow forces the needle upwardly, the flared fluid inlet end thereof is moved to the raised position 30' shown in broken lines in FIG. 1. Back flow then occurs through the passage formed in device 12 and through openings 32 in the needle. In addition, gaps or recesses 38 may be provided in the wall of the passage in device 12, at the level of the upper end of the needle when the needle is in the back flow position, to facilitate the back flush flow of liquid and the removal of blood products.

According to another alternative, two devices according to the invention can be connected to a dialyzer, one at each dialyzer header, and cleaning liquid can be supplied in alternation to each device to quickly remove all blood products.

In those clinics that perform manual cleaning, one or two devices according to the invention can be connected to the dialyzer header(s) as cleaning and disinfecting agents are flushed through the dialyzer. Similarly, one or two devices can be connected to the dialyzer header(s) and the dialyzer can then be placed on an automatic reprocessing machine and processed.

A two way, three port stop cock may be placed between the incoming fluid line and the header cleaning device with the third port exposed to air. Such a stop cock is commercially available from Qosina, Inc. of Edgewood, N.Y. When the stop cock is rotated to circuit the air with the header cleaning device, the water in the header will gravity drain so that the visibility of the header is improved. When rotated to circuit the incoming fluid and the header cleaning device, the incoming fluid forces the needle to rotate within the header and emit a jet transverse to the header. By alternating the stop cock between the incoming fluid line and air, the cleaning of the header and break up of clots will be improved.

In order to prevent any reflux from the dialyzer out the port open to air, a transducer protector, commercially available from companies such as Nextron Medical of New Jersey, can be placed on the port open to air. This transducer permits the flow of air, but not fluids or blood products.

Figure 7:
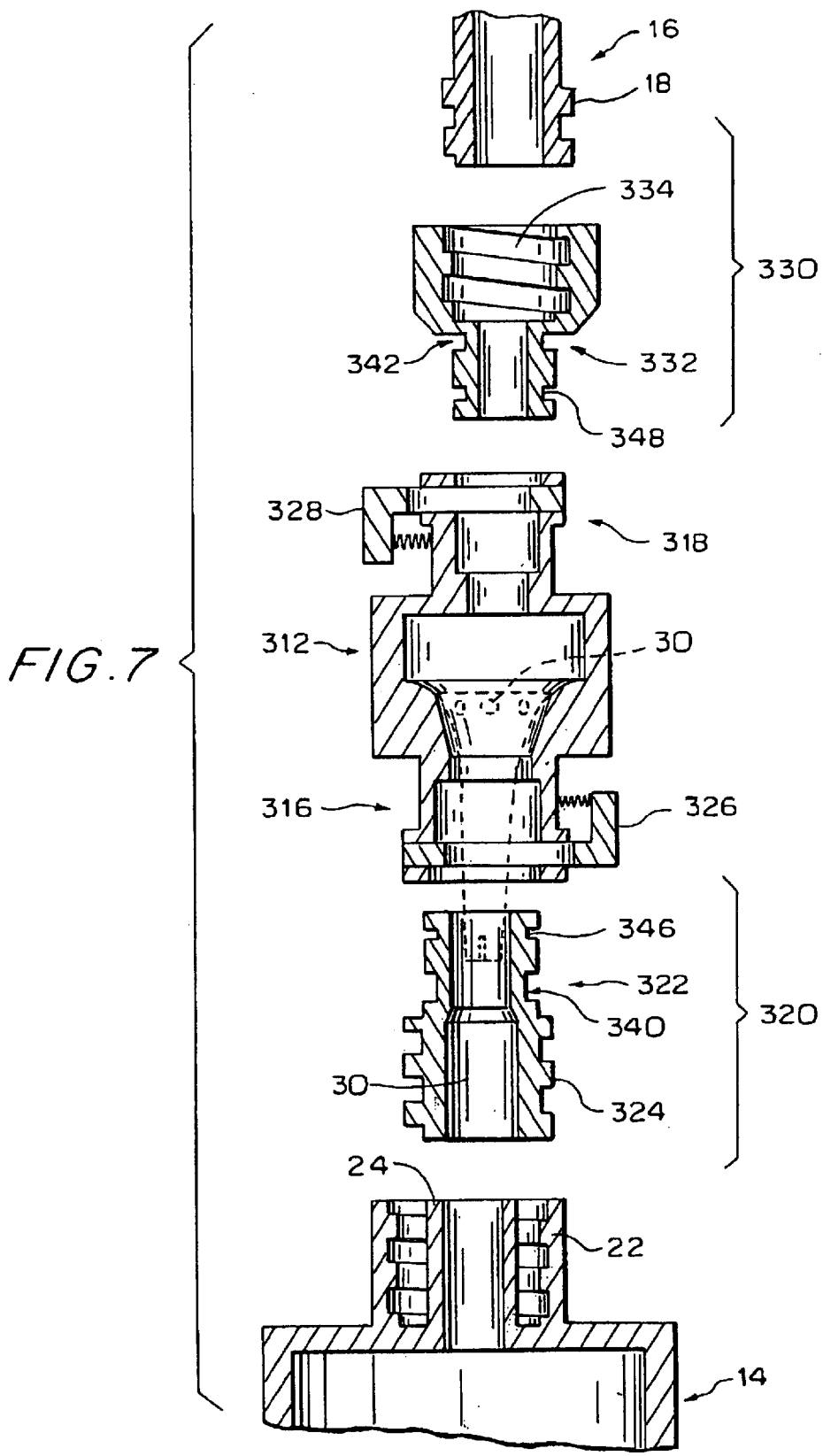
FIG. 7 is an elevational, cross-sectional view illustrating a second preferred embodiment of the invention.

FIG. 7, as mentioned earlier herein, shows a second embodiment of the invention composed of a header cleaning device 312 formed to have a passage essentially identically to the passage provided in device 12 of FIG. 1. Needle 30 is shown in broken lines to indicate its cleaning position without obscuring other features of device 312. The length of needle 30 is not necessarily shown to scale; it will be dimensioned to assure that when all components are assemble, its tip will be properly positioned inside header cap 14. Each end of device 312 is provided with a quick-connect female coupling element 316, 318. A first adapter 320 is provided with a first quick-connect male coupling portion 322 and male threads 324 connectable to the female threads on the inner surface of flange 22 of header cap 14. A second adapter 330 is provided with a second quick-connected male coupling portion 332 and female threads 334 for connection to connector 18 on line 16 for supplying cleaning water or other fluid is provided with.

Each female coupling element 316, 318 is provided with a respective latch member 326, 328 for engagement in a groove 340, 342 of a respective coupling portion 322, 332. Each latch member 326, 328 is provided with a compression spring that urges the respective latch member into it latching position, as shown in FIG. 7. Each male coupling portion 322, 332 is provided with a further groove 346, 348, respectively, for receiving a sealing ring (not shown), such as an O ring.

In order to connect device 312 to header 14, adapter 320 is connected to flange 22, latch member 326 is moved laterally, against the force of it associated spring, to an unlatching position and female coupling element 316 is placed around male coupling portion 322. Then, latch member 326 is released so that one portion thereof engages in groove 340. Similarly, adapter 330 is connected to connector 18 and female coupling element 318 is connected to male coupling portion 332 by moving latch member 328 to its unlatching position and inserting coupling portion 332 into the passage provided in coupling element 318, after which latch member 328 is released so that a portion thereof engages in groove 342. With this arrangement, a fluid tight coupling is provided between device 312 and both the interior of header cap 14 and fluid supply line 16, and device 312 can be rotated manually without interfering with these fluid tight connections. Thus, even if needle 30, or needle 130 or 230, does not spin, the entire interior of header cap 14 can be washed by manual rotation of device 312.

As an alternative to the embodiment shown in FIG. 7, adaptors 320 and 330 can be made integral parts of header cap 14 and line 16, respectively.

A modified version of the device disclosed herein may be usable during dialysis to properly distribute incoming blood into the dialyzer header.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A dialyzer header cleaning device comprising:
   a housing having opposed first and second ends and delimiting a single passage that extends in a flow direction only between the first and second ends;
   a connecting element disposed at said first end of said housing for connection to the header; and
   a flow directing element having a fluid inlet end retained in said passage and a fluid outlet end, said flow directing element being movable by fluid flowing to said fluid inlet into a cleaning position in which said fluid outlet end extends into the header when said first end of said housing is connected to the header and in which fluid can flow through said passage only in one direction toward said first end of said housing, wherein
   said flow directing element is constructed to rotate about an axis that extends in the flow direction in response to a flow of liquid between said fluid inlet end and said fluid outlet end, and to eject at least one liquid stream from said fluid outlet end in a direction transverse to the flow direction.

2. The cleaning device of claim 1 wherein said flow directing element is a needle that tapers from said fluid inlet end towards said fluid outlet end and that has a fluid flow path that extends from said fluid inlet end to said fluid outlet end.

3. The cleaning device of claim 2 wherein said needle has a circular outer wall and an outlet opening via which the fluid streams are ejected in a direction tangential to said outer wall.

4. The cleaning device of claim 3 wherein said needle has formations that project into the fluid flow path and that are configured to produce forces tending to rotate said needle in response to flow of liquid through the fluid flow path.

5. The cleaning device of claim 2 wherein said needle has formations that project into the fluid flow path and that are configured to produce forces tending to rotate said needle in response to flow of liquid through the fluid flow path.

6. The cleaning device of claim 2 wherein said needle has openings in proximity to said fluid inlet end for permitting liquid to flow from the fluid flow path to a region surrounding said needle.

7. The cleaning device of claim 1 wherein said passage tapers in the flow direction and said flow directing element is movable parallel to the flow direction between the cleaning position and a back flush position in response to flow of fluid through said passage from said flow outlet end toward said fluid inlet end to provide a back flush flow path through said passage and around said flow directing element.

8. The cleaning device of claim 7 wherein said flow directing element is a needle that tapers from said fluid inlet end towards said fluid outlet end and that has a fluid flow path that extends from said fluid inlet end to said fluid outlet end.

9. The cleaning device of claim 8 wherein said needle has openings in proximity to said fluid inlet end through which liquid can flow when said needle is in the back flush position.

10. A dialyzer header cleaning device comprising:
    a housing having opposed first and second ends and delimiting a single passage that extends in a flow direction only between the first and second ends;
    a connecting element disposed at said first end of said housing for connection to the header; and
    a flow directing element having a fluid inlet end retained in said passage and a fluid outlet end, said flow directing element having a cleaning position in which said fluid outlet end extends into the header when said first end of said housing is connected to the header, wherein
    said flow directing element is movable parallel to the flow direction between the cleaning position and a back flush position in response to flow of fluid through said passage from said flow outlet end toward said fluid inlet end to provide a back flush flow path through said passage and around said flow directing element only when said flow directing element is in the back flush position.

11. The cleaning device of claim 10 wherein said passage tapers in the flow direction.

12. The cleaning device of claim 11 wherein said flow directing element is a needle that tapers from said fluid inlet end towards said fluid outlet end and that has a fluid flow path that extends from said fluid inlet end to said fluid outlet end.

13. The cleaning device of claim 12 wherein said needle has openings in proximity to said fluid inlet end through which liquid can flow when said needle is in the back flush position.

14. The cleaning device of claim 10 wherein said housing is manually rotatable about an axis that extends in the flow direction when said connecting element is connected to the header and fluid is flowing through said passage.

* * * * *